US00PP23628P3

(12) United States Plant Patent
Egger

(10) Patent No.: US PP23,628 P3
(45) Date of Patent: May 21, 2013

(54) ***TIARELLA* PLANT NAMED 'SUNSET RIDGE'**

(50) Latin Name: ***Tiarella* spp.**
Varietal Denomination: Sunset Ridge

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 92 days.

(21) Appl. No.: 13/200,476

(22) Filed: Sep. 22, 2011

(65) Prior Publication Data

US 2013/0081187 P1 Mar. 28, 2013

(51) Int. Cl.
*A01H 5/00* (2006.01)

(52) U.S. Cl.
USPC ..... Plt./486

(58) Field of Classification Search ..... Plt./486
See application file for complete search history.

*Primary Examiner* — Susan McCormick Ewoldt

(74) *Attorney, Agent, or Firm* — Klarquist Sparkman, LLP

(57) ABSTRACT

A new and distinct cultivar of *Tiarella* plant characterized by glossy leaves, large, ovate leaves with prominent dark markings along the veins and in splatters away from the veins, an excellent trailing habit, and excellent vigor.

1 Drawing Sheet

Botanical denomination: *Tiarella* spp.
Variety designation: 'Sunset Ridge'.

BACKGROUND OF THE INVENTION

The present invention relates to a new and distinct cultivar of a hardy herbaceous perennial of the genus *Tiarella*, and known by the cultivar name 'Sunset Ridge'. The genus *Tiarella* is a member of the family Saxifragaceae.

The new cultivar originated from a planned breeding program as a cross between *Tiarella* 32-01 as the seed parent and *Tiarella* 37-09, as the pollen parent. Both parents are proprietary, unreleased *Tiarella*.

Compared to *Tiarella* 'Appalachian Trail' (U.S. Plant Pat. No. 22,675), the new cultivar has leaves that are glossy and larger.

SUMMARY OF THE INVENTION

This plant is uniquely characterized by the following:

1. glossy leaves,
2. large, ovate leaves with prominent dark markings along the veins and in splatters away from the veins,
3. an excellent trailing habit,
4. and excellent vigor.

The new variety has been reproduced only by asexual propagation (cuttings and micropropagation). Each of the progeny exhibits identical characteristics to the original plant. Asexual propagation by cuttings and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the foliage of *Tiarella* 'Sunset Ridge' in July from plants grown indoors.

FIG. 2 shows *Tiarella* 'Sunset Ridge' growing outside in the garden in a 10" hanging basket in August in Canby, Oreg.

DETAILED PLANT DESCRIPTION

The following is a detailed description of the new *Tiarella* cultivar based on observations of 6-month-old plants grown in one gallon containers in a warm greenhouse in April in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart, 5$^{th}$ edition.

Plant:
- *Type.*—Herbaceous perennial.
- *Hardiness.*—USDA Zones 4 to 9.
- *Form.*—Trailing.
- *Size.*—38 cm wide and 16 cm high from the soil to the top of the foliage.
- *Vigor.*—Excellent.
- *Roots.*—Fibrous, freely branching, fine, and white in color; roots develop easily from stem cuttings.

Stem:
- *Type.*—Decumbent with adventitious roots at the nodes.
- *Size.*—Grows to 3 mm wide and 30 cm long.
- *Surface.*—Pubescent.
- *Internodes.*—1.5 cm to 3 cm long.
- *Color.*—Closest to Brown 200C.

Leaves:
- *Type.*—Simple.
- *Arrangement.*—Rosette.
- *Shape.*—Broadly ovate.
- *Lobing.*—5 shallow lobes, terminal lobe the longest, all with secondary lobes.
- *Margins.*—Crenate.
- *Venation.*—Palmate.
- *Apex.*—Acute.
- *Base.*—Cordate, strongly overlapping.
- *Blade.*—Grows to 13 cm long and 11.5 cm wide.

*Surface.*—Hispid top and bottom, glossy.

*Petiole description.*—7 to 12 cm long and 2.5 mm wide, hirsute, Grey Brown N199B.

*Leaf color.*—Topside, Green 137A with the leaf center pattern Greyed Purple N187A; bottom side Yellow Green 147B with markings tinted Greyed Purple N187A.

Inflorescence:

*Type.*—Raceme.

*Flower number.*—About 30 per raceme.

*Size of inflorescences.*—Grows to 11.5 cm long and 2.5 cm wide.

*Number of inflorescences.*—8 in first spring flush.

*Bloom period.*—March to mid June in Canby, Oreg.

*Peduncle.*—Unbranched, grows to 21 cm long and 2 mm wide at the base, hispid, Brown N199A.

*Pedicel.*—6 mm long and 1 mm wide, hispid, Brown N199A.

*Lastingness.*—A raceme blooms for about 3 weeks.

Flower bud:

*Size.*—4 mm deep and 2.5 mm wide.

*Description.*—Ovoid, down facing until open.

*Surface.*—Glandular.

*Color.*—Light pink, White N155B.

Flower:

*Type.*—Perfect, actinomorphic, sepals petaloid.

*Shape.*—Rotate.

*Flower size.*—7 mm wide and 6 mm deep including stamens and pistil.

*Corolla.*—5 petals, each 3 mm long and 1 mm wide, lanceolate with a clawed base, margin entire, tip acuminate, glabrous on both sides, White NN155D inside and outside.

*Calyx.*—6 mm wide and 1.5 mm deep, 5 sepals, backs glandular, inside glabrous, petaloid, parted almost to the base; lobes obovate, tips obtuse, margins entire, 2 mm long and 1.5 mm wide, White NN155C.

*Stamens.*—10, conspicuously exerted; filaments 5 mm long, White NN155D; anthers undehisced Orange Red 31D; pollen Yellow Orange 22B.

*Pistil.*—1, White N155B, 5 mm long and 2 mm wide, ovary 2 mm long and 2 mm wide, glandular.

*Fragrance.*—None.

Fruit and seed: 6 mm long and 2.5 mm wide, Yellow Green 146C with little seed set; seed Brown 200A, oval, 1.5 mm long Pest and disease resistance: This new hybrid shows good mildew tolerance, the main problem for *Tiarella*. No major pest problems. It is susceptible to root weevils, like all *Tiarella*.

I claim:

1. A new and distinct cultivar of *Tiarella* plant herein illustrated and described.

* * * * *

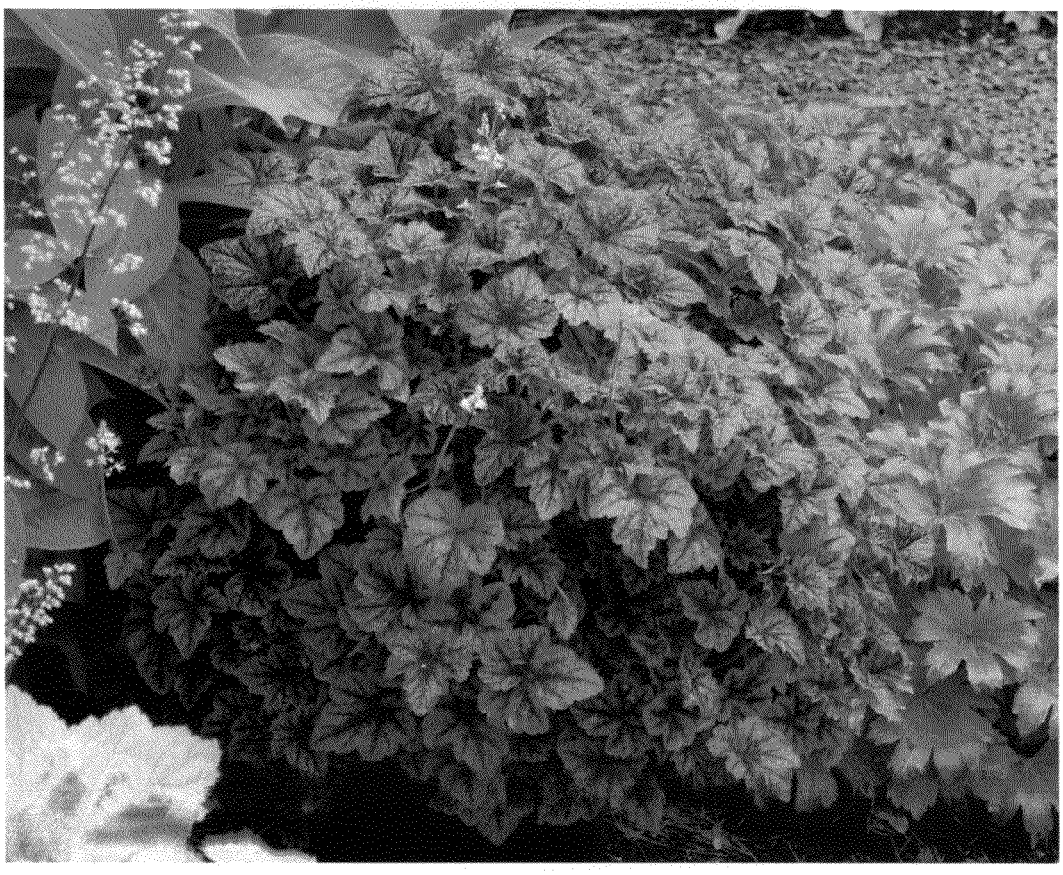

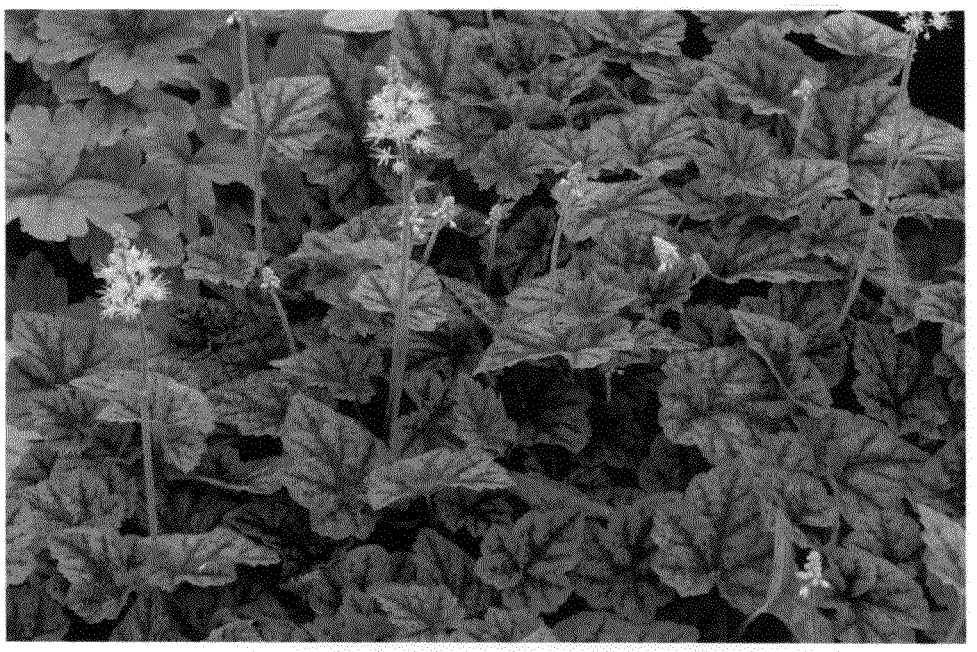
FIG.1 above, FiG. 2 below